(12) United States Patent
Tao

(10) Patent No.: US 8,859,761 B2
(45) Date of Patent: Oct. 14, 2014

(54) REFINING PROCESS OF CEFAMANDOLE SODIUM

(75) Inventor: Linggang Tao, Wuyi County (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 13/885,625

(22) PCT Filed: Mar. 17, 2011

(86) PCT No.: PCT/CN2011/000435
§ 371 (c)(1),
(2), (4) Date: May 15, 2013

(87) PCT Pub. No.: WO2012/100383
PCT Pub. Date: Aug. 2, 2012

(65) Prior Publication Data
US 2013/0303754 A1    Nov. 14, 2013

(30) Foreign Application Priority Data

Jan. 28, 2011 (CN) .......................... 2011 1 0032273

(51) Int. Cl.
*C07D 501/12*    (2006.01)
*C07D 501/36*    (2006.01)
*A61K 31/546*    (2006.01)
*C07D 501/58*    (2006.01)

(52) U.S. Cl.
CPC ............ *C07D 501/58* (2013.01); *A61K 31/546* (2013.01); *C07D 501/36* (2013.01)
USPC .......................................... 540/220; 540/226

(58) Field of Classification Search
USPC ................................... 540/226, 220; 548/251
See application file for complete search history.

(56) References Cited

U.S. PATENT DOCUMENTS 4,115,644 A    9/1978    Chou et al.

FOREIGN PATENT DOCUMENTS

| CN | 101279979 A | 10/2008 |
|---|---|---|
| CN | 101787036 A | 7/2010 |
| EP | 0432297 A | 6/1991 |

*Primary Examiner* — Golam M M Shameem
*Assistant Examiner* — Laura Daniel
(74) *Attorney, Agent, or Firm* — CBM Patent Consulting, LLC

(57) ABSTRACT

It discloses a novel process for refining cefamandole nafate, comprising: 1) adsorbing cefamandole nafate with strongly acidic ion exchange resin, followed by eluting the resin and collecting the eluate, to provide a primary purified cefamandole acid after concentration under reduced pressure; 2) neutralizing the primary purified cefamandole acid with an aqueous solution of sodium hydroxide or an aqueous solution of basic salt of sodium, followed by adjusting the pH value and filtrating out the insoluble substances with heating, thereby providing a secondary purified aqueous solution of cefamandole nafate; and 3) adding ethanol in a volume ratio between ethanol and water of 4:6 into the aqueous solution, to allow recrystallization under controlling the temperature, to provide a tertiary purified cefamandole nafate. The refined cefamandole nafate product has a purity of no less than 99.5%, mostly no less than 99.6%, with significantly low content of heavy metals.

13 Claims, No Drawings

REFINING PROCESS OF CEFAMANDOLE SODIUM

FIELD OF THE INVENTION

The invention relates to medical technology, in particular, to a novel process for refining cefamandole nafate.

PRIOR ART

Cefamandole nafate is a second-generation cephalosporin antibiotic developed originally by Lilly Company (US), having the chemical name sodium 7-D-(2-formyloxy phenyl acetamide)-3-[(1-methyl-1H-tetrazol-5-yl)thiomethyl]-3-cephem-4-carboxylate, and a formula of $C_{19}H_{17}N_6NaO_6S_2$. It has a molar weight of 512.50 and the following structure:

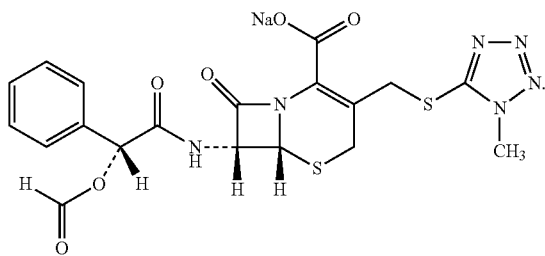

Cefamandole nafate is a prodrug of Cefamandole. It is rapidly hydrolyzed to Cefamandole after coming into the body. Therefore, both of them have essentially same antimicrobial function in vivo. Cefamandole nafate shows high antimicrobial activity against gram-negative bacteria, higher antimicrobial activities against anaerobic *clostridium*, meningococcus, gonococcus, *escherichia coli*, pneumobacillus, *Bacillus* influenzae as well as indole-positive proteus, and especially most highest effect against *Haemophilus*. It is clinically useful mainly for the treatment of various infections induced by sensitive bacteria, such as respiratory tract infections, infections of biliary tract, nephropyelitis, urinary tract infections, peritonitis, blood poisoning, as well as skin and soft tissues infections, infections of bone, joint infections and so on.

A number of references of patents and journals have disclosed cefamandole nafate and processes for preparing the same.

U.S. Pat. No. 4,351,947 discloses that cefamandole nafate is obtained as follows: formyl mandelic acid is reacted with 1-methyl-5-mercapto-1,2,3,4-tetrazole to give an active ester, which is reacted with 7-ACA or 7-amino-3-(1-methyl-1H-tetrazol-5-yl)-thiomethyl-3-cephem-4-carboxylic acid (7-ATCA) to obtain an acid of Cefamandole, which is saltified to give cefamandole nafate. The process of this method is complex. Materials with higher toxicity and anaphylaxis such as DCC and so on are used in the process, thereby there is need of severe labour protection in the production. In addition, total yield of syntheses, about 72%, is not high, and the quality of product is also not stabile.

European patent EP0432297 discloses the synthesis of cefamandole nafate using acyl chloride, wherein 7-TCA is reacted with 1-methyl-5-mercapto-1,2,3,4-tetrazole to obtain 7-ATCA, which is subjected to silylation protection and then acylation reaction with D-(-)-2-formyloxy-2-phenyl acetyl chloride, and after hydrolysis, decolourization and salification, is separated to give a solid of cefamandole nafate. In this method, ammonia formed as a byproduct during the silylation needs to be exhausted as possible from the reaction system of silylation, otherwise the process of silylation will be influenced. Moreover, in the method, additional acid-binding agent is added during the acetylation to neutralize hydrogen chloride produced. N,N-dimethyl aniline used as the acid-binding agent has toxicity for causing a cancer. And in the process, it is needed to firstly separated an acid of Cefamandole alone, which is additional operation step and decreases the yield, thus the production cost of this product is increased.

Although these processes can produce cefamandole nafate effectively, the purity of the targeted product is not high, the color is not well and the content is low, which influences the quality of its preparation. Such processes provided for treating or purifying products are conventional in organic synthesis, and the increase of purity is limited. Therefore, many companies and development departments have developed several purifying and refining processes for cefamandole nafate.

In Medicament of Heilongjiang, 2000, 12(5), a process for refining cefamandole nafate is reported, in which cefamandole nafate is reacted with ethyl dl-lactic acid, then is dissolved, failed out as a crystal, which is then separated with ethanol to give cefamandole nafate with a purity of 96.9%. However, this process is very complicated, and the production cost will surely increase greatly when the process in used in large scale. Meanwhile, it is difficult to control the quality.

Chinese patent CN101279979 (granted as CN101279979B) discloses a separation and purification process of cefamandole nafate and a preparation method of freeze-dried injectable powder, which comprises conducting high-speed countercurrent chromatography for three times, which uses trichloromethane, ethyl acetate, methanol and water as the solvent system of immobile phase and mobile phase. The upper is immobile phase and the low is mobile phase. However, trichloromethane will be left in trace amount, which is dangerous for latter use. Furthermore, it is difficult to separate the impurities dissolved in the mixture of such solvents, and the increases in yield and purity are limited.

Chinese patent CN101787036A discloses a compound of cefamandole nafate with high purity, which is obtained from a process comprising the following steps: (1) reacting cefamandole sodium (namely cefamandole nafate) with an acid to fall out insoluble cefamandole acid; (2) dissolving cefamandole acid into a solvent, treating with macroporous absorption resin, eluting and purifying with a solvent, recovering the eluate and filtrating; (3) reacting purified cefamandole acid with an alkaline to give cefamandole nafate. Although this process can improve the purity of cefamandole nafate, as for cefamandole nafate, which is a high polar compound, the purification efficiency of neutral resin such as Hp-20 resin is not high. Moreover, additional negative ionic impurities will be brought in during the process of adjusting of the pH value, which increases the difficulty of separation.

DETAILED DESCRIPTION OF THE INVENTION

The invention provides a process for refining cefamandole nafate, which overcomes the above defects existing in the prior art, especially the low purity of cefamandole nafate producted in the prior art.

The cefamandole nafate useful in the present refining process can be crude cefamandole nafate obtained from any known process in the art for preparing cefamandole nafate or any commercially available cefamandole nafate drug substance, hereinafter all referred to as cefamandole nafate material used according to the present invention.

After intensive study, the inventor surprisingly found that the purity of cefamandole nafate material can be substantially improved by a refining process which comprises the steps of:

1) adsorbing cefamandole nafate with strongly acidic ion exchange resin, followed by eluting the resin and collecting the eluate, to provide a primary purified cefamandole acid after concentration under reduced pressure;

2) neutralizing the primary purified cefamandole acid with an aqueous solution of sodium hydroxide or an aqueous solution of basic salt of sodium, followed by adjusting the pH value and filtrating out the insoluble substances with heating, thereby providing a secondary purified aqueous solution of cefamandole nafate; and 3) adding ethanol in a volume ratio between ethanol and water of 4:6 into the aqueous solution, to allow recrystallization under controlling the temperature, to provide a tertiary purified cefamandole nafate.

The invention is further illustrated as follows.

Step 1)

It should be noticed that the process for refining cefamandole nafate as disclosed in CN101787036A is carried out in two steps: crude cefamandole nafate is treated with an acid to adjust the pH value, and then purified through macroporous absorption resin to collect the eluate. In addition to the complicated operations, additional negative ions can be introduced by adjusting the pH value. Such a neutral resin as D1300 or BS-55 macroporous absorption resin does not exhibit a satisfactory purification efficiency for cefamandole acid (or its sodium salt) with a high polarity. The use of strongly acidic ion exchange resin can efficiently overcome these drawbacks, and two steps, adjusting with an acid and passing through the resin, are combined and carried out in one step.

In step 1) of the present invention, cefamandole nafate is adsorbed onto the strongly acidic ion exchange resin and then eluted, after which the eluate is collected and concentrated under reduce pressure to give a primary purified cefamandole acid.

In general, an ion exchange resin with sulfonic acid group in the polymeric substrate of crosslinked structure is known as strongly acidic ion exchange resin, which shows acidity by dissociation of hydrogen ion. It's strength of acidity is corresponding to that of an inorganic acid such as sulfuric acid, hydrochloric acid and so on, and shows ion exchange function in basic, neutral, or even acidic medium. Common strongly acidic ion exchange resin is based on styrene-divinylbenzene copolymer spherical particles and is obtained from sulfonating above copolymer spherical particles with concentrated sulfuric acid, fuming sulfuric acid, chlorosulfonic acid and so on.

Generally, cefamandole nafate material contains solvents, various raw materials and intermediate products, which are introduced during the preparation, and also contains moisture due to hygroscopicity, bacterial endotoxin, and various inorganic substances and heavy metals, and so on. Theses substances are present in the form of impurities which affect the purity of cefamandole nafate. The strongly acidic resins used in the present invention have the general functions as ion exchange resins do. When the strongly acidic resin is contacted with a solution containing cefamandole nafate, in addition to playing a role of ion exchange, it can adsorb non-electrolyte substances from the solution and thus can adsorb the residual impurities. In addition, the resin itself has a bleaching effect to remove any impurity that can endow others a color, and such effect is better than that of activated carbon.

The invention can use common strongly acidic ion exchange resins, such as strongly acidic styrenic cation exchange resins of D001, strongly acidic styrenic cation exchange resins of GB/T 13659-2008 001×7, and so on. All these strongly acidic cation resins are commercially available. Of course, macroporous strongly acidic ion exchange resins with other trade names can also be used.

According to the present invention, cefamandole nafate-containing solution can pass through the strongly acidic cation resin in a continuous or non-continuous process. Specifically, the useful processes include batch process, fixed bed process and continuous process.

The batch process is carried out in a reaction tank. The exchange solution flows into the tank from the bottom, and the ion exchange equilibrium is accelerated by continuously introducing a gas to fluidize the resin or by stirring. The exchange process is stopped after the equilibrium is achieved, and then the solution is released from the bottom.

In a fixed bed process, the ion exchange resin is packed into an exchange column to form a resin bed, and then a solution is introduced for processing. During a fixed-bed operation, the solution typically flows from top to bottom in a manner as forward flow, or from bottom to top in a countercurrent regeneration manner, i.e. flowing in the opposite direction against the exchange solution. A convection-type counter-current manner can also be useful.

A solution containing 0.1 g Cefamandole per 1 ml water has pH value between 4.0 and 6.5 since cefamandole nafate carries carboxyl group and has high polarity per se. The pH value can be decreased after cefamandole nafate passing through strongly acidic ion exchange resin and sodium ion is exchanged with hydrogen ion to give cefamandole acid.

When an equilibrium is reached, the adsorbed cefamandole acid is eluted after being eluted with a common solution of hydrochloric acid or sulfuric acid (called resin regeneration). The eluate is collected, and concentrated under a reduced pressure.

Step 2)

Neutralizing with an aqueous solution of sodium hydroxide or an aqueous solution of basic salt of sodium, followed by adjusting the pH value and filtrating out the insoluble substances with heating, thereby providing a secondary purified aqueous solution of cefamandole nafate.

According to the invention, basic salt of sodium used in this step is one or more preferably selected from a group consisting of sodium carbonate, sodium bicarbonate, sodium formate, sodium acetate, sodium propionate and sodium benzoate.

According to the invention, in this step, the pH value is adjusted to weak acidity to weak alkaline, such as from 5 to 9, preferably from 6 to 8, most preferably from 6.5 to 7.5.

Cefamandole nafate is dissolved completely in heat solution, and insoluble substances are removed out with heating, thereby the purity of cefamandole nafate is further increased.

Without being bound to any theory, neutralizing cefamandole acid with sodium hydroxide or basic salt of sodium in step 2) of the invention can achieve a purification effect probably due to the following reasons:

In the process of CN101787036A for preparing cefamandole nafate, after being absorbed with macroporous resins, the obtained cefamandole acid reacts with a base to give cefamandole nafate. Since it is easy for cefamandole nafate to be dissolved in water, the pH value should be exactly controlled in order to obtain cefamandole nafate from an aqueous solution. Furthermore, insoluble substances will inevitably been carried away if they are not been filtered off. While in step 2) of the invention, aqueous solution of cefamandole nafate is formed directly, and insoluble substances are removed out with heating, thereby the purity is further increased.

Step 3)

Ethanol in a volume ratio between ethanol and water of 4:6 is added into the aqueous solution, and recrystallization is carried out under controlling the temperature, to provide a tertiary purified cefamandole nafate.

The inventors study and find that, as for cefamandole nafate, employing refluence in general single solvent, or recrystallizing at reduced temperature, or suspending in a solvent and stirring under reflux, it is difficult to crystallize, or the content of precipitated impurities is high. Furthermore, it is impossible to achieve expected purity to separate crude cefamandole nafate directly using a separating method with good and bad solvent(s).

Cefamandole nafate dissolves well in water, whereas is almost insoluble in ethanol. It is possible for cefamandole nafate to recrystallize from a mixture of water and ethanol as the solvent. Surprisingly, after inventive treatments described in above steps 1) and 2), through adding ethanol into the obtained aqueous solution of cefamandole nafate, when the volume ratio between ethanol and water in the solvent mixture is 4:6, the obtained solution of cefamandole nafate can recrystallize under reduced temperature to obtain crystals with very high purity. The reason may be that the impurities having an adverse effect on the recrystallization have been removed through steps 1) and 2) according to the invention, and moreover after adjusting the pH value with an alkaline, it is more suitable for cefamandole nafate to recrystallize from the solvent mixture.

During the recrystallization, cefamandole nafate firstly is dissolved in water as little as possible under increased temperature, such as from 60 to 100° C., and the excess water is vaporized off. Then ethanol in a volume ratio between ethanol and water of 4:6 is added into the aqueous solution. Then, the temperature is gradually cooled down until it is between room temperature and 10° C., while crystals gradually precipitate. Seed crystals of Cefamandole nafate are optionally added during the cooling process. The crystallization is complete after standing still for 5-20 hours, and then drying in a way such as air drying or drying in an oven is carried out. It is preferable to dry in an oven and the temperature of the oven is from 100 to 160° C.

EMBODIMENTS OF THE INVENTION

The invention provides a process for refining cefamandole nafate, characterized in comprising the steps of:

1) adsorbing cefamandole nafate with strongly acidic ion exchange resin, followed by eluting the resin with a solution of hydrochloric acid or sulfuric acid, collecting the eluate, and concentrating under reduced pressure;

2) neutralizing with an aqueous solution of sodium hydroxide or an aqueous solution of basic salt of sodium, followed by adjusting the pH value to weak acidity to weak alkaline, such as from 5 to 9, preferably from 6 to 8, most preferably from 6.5 to 7.5, and filtrating out the insoluble substances with heating; and 3) adding ethanol in a volume ratio between ethanol and water of 4:6 into the aqueous solution of cefamandole nafate with the temperature of 60-100° C., gradually cooling down until the temperature is between room temperature and 10° C. to allow recrystallization.

In an embodiment of the invention, in step 1), after cefamandole nafate is adsorbed onto the acidic ion exchange resin and exchanged with it, the acidic solution used to elute may be a solution of hydrochloric acid or sulfuric acid with any concentration, preferably diluted aqueous solution of hydrochloric acid or sulfuric acid, preferably the concentration of hydrochloric acid is from 5 to 37%, more preferably from 10 to 20%, and the concentration of sulfuric acid general is <70%, preferably from 30 to 60%, most preferably from 40 to 50%. Normally, nitric acid is not used since it is not easy to remove the nitrate off.

In an embodiment of the invention, in step 2), the temperature at which filtrating with heating is from 30 to 90° C., preferably from 40 to 80° C., more preferably from 50 to 70° C.

In an embodiment of the invention, step 2) is followed by step 3), while cefamandole nafate is dissolved in water. It is general that cefamandole nafate is dissolved in water after filtrating with heating in step 2), or the aqueous solution of cefamandole nafate is further heated, preferably until arriving at 70 to 90° C., in order to further vaporize the moisture. Optionally the solution is filtered with heating one time more in order to remove the present insoluble substances off. Absolute ethanol with a volume ratio between ethanol and water of 4:6 is added in batch while the temperature is cooled down, and is added completely when the temperature arrives at 50° C. When the temperature is cooled down to 10 to 15° C., crystals gradually precipitate.

The refined cefamandole nafate obtained from above embodiments has a purity of no less than 99.5%, mostly no less than 99.7%, measured by High Performance Liquid Chromatography.

The refined cefamandole nafate according to the invention contains heavy metals at very low content.

Since the powder flowability, specific dissolution rate, solid stability of cefamandole nafate and the operatablitity of the process play important roles in the activity of cefamandole nafate and the preparations thereof, cefamandole nafate with substantially increased purity brings about a significant improvement in the dissolution rate, the formulatability and the stability.

Therefore, the refined cefamandole nafate according to the inventive process is highly suitable for formulating an antimicrobial pharmaceutical composition for the treatment of various infections due to gram-negative bacteria, wherein the pharmaceutical composition comprises the refined cefamandole nafate according to the inventive process and pharmaceutically acceptable excipients. Preferably, the pharmaceutical composition can be freeze-dried powder. The invention also provides a use of the pharmaceutical composition in the preparation of a antimicrobial medicine for the treatment of various infections due to gram-negative bacteria; and the above infections preferably includes respiratory tract infection, infections of biliary tract, nephropyelitis, urinary tract infections, peritonitis, blood poisoning, as well as skin and soft tissues infections, infections of bone, joint infections and so on.

The present invention has fundamentally enhanced the lower purity of the current crude cefamandole nafate, solved the problem existing in crude cefamandole nafate and cefamandole nafate drug substances, reduced a series of clinical adverse reactions due to the presence of excessive impurities. In addition, the present invention yields cefamandole nafate in a high ratio and a high purity of no less than 99%, mostly no less than 99.2%, with a overall yield of no less than 92%. The present invention also has advantages of convenience, easy to control and industrialization.

The following examples are intended to further explain or illustrate the invention, and the examples provided should not be understood as limiting the scope of the invention.

D001 strongly acidic styrene cation exchange resin and GB/T 13659-2008 001×7 strongly acidic styrene cation exchange resin used in the examples are available resin useful in industry.

I. Measurement of the Purity for Cefamandole Nafate

High Performance Liquid Chromatography is used to measure the purity of cefamandole nafate sample.

II. Measurement of the Content of Heavy Metals 1.0 g of cefamandole nafate sample was taken and examined according to the regulations (Chinese Pharmacopoeia 2, Appendix VIII H, Method II, the 2000 edition). The content of heavy metals was normally required as no more than 10 ppm.

EXAMPLE 1

10 g of cefamandole nafate with a purity of 95%, prepared according to U.S. Pat. No. 4,351,947A, was weighted exactly. The solution containing cefamandole nafate was loaded into a fixed bed filled with D001 strongly acidic styrene-based cation exchange resin before the exchange proceeded until the pH value was adjusted to 3.3. Then an elution was performed using 10% aqueous solution of hydrochloric acid as the eluent to obtain an eluate which was collected and concentrated under reduced pressure. At this time, the purity was examined by HPLC as 97.5%. The pH value was adjusted to 6.8 with 1M aqueous solution of sodium hydroxide while the temperature was raised to 50° C., and filtered out the insoluble substances with heating. At this time, the purity was examined by HPLC as 98.4%.

The temperature was raised to 70° C. and keeping for 20 minutes, in order to vaporize excessive moisture from the solution of cefamandole nafate. Then absolute ethanol in a volume ratio between ethanol and water of 4:6 was added in batch, and the temperature was gradually cooling down. The residual ethanol was added completely when the temperature arrived at 50° C. When the temperature is cooled down to room temperature, crystals gradually precipitate. After standing still for 20 hours, the crystallization was completed, then the crystals are dried in an oven at a temperature of 120° C. to provide 9.5 g of refined cefamandole nafate with a yield of 95%.

The purity was measured as 99.8% by HPLC and the content of heavy metals was 6 ppm.

COMPARATIVE EXAMPLE 1

Crude product of cefamandole nafate with a purity of 95%, prepared according to U.S. Pat. No. 4,351,947A, was purified according to the refining process as described in Chinese patent CN101279979A. 2 g of crude cefamandole nafate was separated and purified for three times by high-speed countercurrent chromatography, where trichloromethane, ethyl acetate, methanol and water were used as the solvent system of immobile phase and mobile phase. The upper is immobile phase and the low is mobile phase. White β-typed refined cefamandole nafate was obtained. The purity was measured as 98.2% by HPLC and the content of heavy metals was 25 ppm.

EXAMPLE 2

10 g of cefamandole nafate drug with a purity of 97% was weighted exactly. The solution containing cefamandole nafate was loaded into a fixed bed filled with D201 strongly acidic styrene-based cation exchange resin before the exchange proceeded until the pH value was adjusted to 2.8. Then an elution was performed using 50% solution of sulfuric acid as the eluent to obtain an eluate which was collected and concentrated under reduced pressure. The purity was measured by HPLC as 98.5%.

The pH value was adjusted to 7.5 with 2M aqueous solution of sodium carbonate while the temperature was raised to 65° C., and filtered out the insoluble substances with heating. At this time, the purity was measured by HPLC as 99.1%.

The temperature was raised to 80° C. and keeping for 30 minutes, in order to vaporize excessive moisture from the solution of cefamandole nafate. Then absolute ethanol in a volume ratio between ethanol and water of 4:6 was added in batch, and the temperature was gradually cooling down, the residual ethanol was added completely when the temperature arrived at 55° C. When the temperature is cooled down to 15° C., crystals gradually precipitate. After standing still for 15 hours, the crystallization was completed, then the crystals are dried in an oven at a temperature of 140° C. to provide 9.6 g of refined cefamandole nafate with a yield of 96%.

The purity was measured as 99.8% by HPLC and the content of heavy metals was 5 ppm.

COMPARATIVE EXAMPLE 2

Cefamandole nafate drug with a purity of 97% was purified according to the refining process as described in Chinese patent CN101787036A. Firstly, cefamandole sodium was reacted with an acid to fall out insoluble cefamandole acid; which then was dissolved into a solvent, treated with macroporous absorption resin, eluted and purified with a solvent, recovered the eluate and filtered. Lastly the purified cefamandole acid was reacted with an alkaline to give cefamandole nafate. The purity was measured as 98.5% by HPLC and the content of heavy metals was 35 ppm.

EXAMPLE 3

10 g of crude cefamandole nafate with a purity of 96%, prepared according to EP0432297, was weighted exactly. The solution containing cefamandole nafate was loaded into a reactor filled with GB/T 13659-2008 001×7 strongly acidic styrene-based cation exchange resin, and $CO_2$ gas is introduced for promoting the exchange, until the pH value was adjusted to 3.1. Then an elution was performed using 15% aqueous solution of hydrochloric acid as the eluent to obtain an eluate which was collected and concentrated under reduced pressure. At the time, the purity was measured by HPLC as 97.9%.

The pH value was adjusted to 6.6 with 1M aqueous solution of sodium acetate while the temperature was raised to 60° C., and filtered out the insoluble substances with heating. At this time, the purity was measured by HPLC as 98.8%.

The temperature was raised to 80° C. and keeping for 15 minutes, in order to vaporize excessive moisture from the solution of cefamandole nafate. Then absolute ethanol in a volume ratio between ethanol and water of 4:6 was added in batch, and the temperature was gradually cooling down, the residual ethanol was added completely when the temperature arrived at 50° C. When the temperature is cooled down to room temperature, crystals gradually precipitate. After standing still for 25 hours, the crystallization was completed, then the crystals are dried in an oven at a temperature of 130° C. to provide 9.6 g of refined cefamandole nafate with a yield of 96%.

The purity was measured as 99.7% by HPLC and the content of heavy metals was 8 ppm.

EXAMPLE 4

10 g of cefamandole nafate drug with a purity of 98% was weighted exactly. The solution containing cefamandole nafate was loaded into a fluidized bed filled with GB/T 13659-2008 001×7 strongly acidic styrene-based cation exchange resin before the exchange proceeded until the pH value was adjusted to 2.5. Then an elution was performed using 30% solution of sulfuric acid as the eluent to obtain an eluate which was collected and concentrated under reduced pressure. At the time, the purity was measured by HPLC as 99.1%.

The pH value was adjusted to 8.0 with 2M aqueous solution of sodium hydroxide while the temperature was raised to 50° C., and filtered out the insoluble substances with heating. At this time, purity was measured by HPLC as 99.5%.

The temperature was raised to 90° C. and keeping for 30 minutes, in order to vaporize excessive moisture from the solution of cefamandole nafate. Then absolute ethanol in a volume ratio between ethanol and water of 4:6 was added in batch, and the temperature was gradually cooling down, the residual ethanol was added completely when the temperature arrived at 60° C. When the temperature is cooled down to 10° C., crystals gradually precipitate. After standing still for 20 hours, the crystallization was completed, then the crystals are dried in an oven at a temperature of 150° C. to provide 9.7 g of refined cefamandole nafate with a yield of 97%.

The purity was measured as 99.9% by HPLC and the content of heavy metals was 4 ppm.

The invention has been already illustrated according to the above examples. The foregoing examples are only intended to exemplify the invention. It will be appreciated that numerous modifications and embodiments may be devised by the skilled in the art without deviating the spirit and essence of the invention. Such modifications are also understood to fall within the scope of the invention.

What is claimed is:

1. A process for refining cefamandole nafate comprising the following steps:
    1) loading a cefamandole nafate into an ion exchange resin with sulfonic acid group in a polymeric substrate of cross-linked structure, followed by eluting the resin, and collecting the eluate concentrated by a reduced pressure to produce a primary purified cefamandole acid;
    2) neutralizing the primary purified cefamandole acid with an aqueous solution of sodium hydroxide or an aqueous solution of basic salt of sodium, followed by adjusting the pH and removing insoluble substances with heat, which yields a secondary purified aqueous solution of cefamandole nafate; and
    3) producing a tertiary purified cefamandole nafate by adding ethanol into the secondary purified aqueous solution of cefamandole nafate at the ratio of 4:6 for the ethanol to the secondary purified aqueous solution by volume and by recrystallizing with adjusting temperature.

2. The process for refining cefamandole nafate according to claim 1, characterized in that, the pH in step 1) is decreased after said cefamandole nafate passes through the acidic ion exchange resin.

3. The process for refining cefamandole nafate according to claim 1, wherein the basic salt of sodium used in step 2) is one or more selected from a group consisting of sodium carbonate, sodium bicarbonate, sodium formate, sodium acetate, sodium propionate and sodium benzoate.

4. The process for refining cefamandole nafate according to claim 3, wherein the basic salt of sodium used in step 2) is sodium carbonate or sodium acetate.

5. The process for refining cefamandole nafate according claim 1, wherein the pH value in step 2) is adjusted to a range between 5 to 9.

6. The process for refining cefamandole nafate according to claim 1, wherein the temperature in step 2) is set by the heat at a range between 30 and 90° C. for removing the insoluble substances.

7. The process for refining cefamandole nafate according to claim 1, wherein adding the ethanol of step 3) in batches which is completed when the temperature is adjusted to 50° C., then adjusting the temperature down to a range between room temperature and 10° C.

8. The process for refining cefamandole nafate, comprising the following steps:
    1) loading cefamandole nafate into an acidic ion exchange resin with sulfonic acid group in a polymeric substrate of cross-linked structure, followed by eluting the resin with a solution of hydrochloric acid or sulphuric acid, and collecting eluate concentrated by said reduced pressure;
    2) neutralizing the eluate obtained at step 1) with an aqueous solution of sodium hydroxide or an aqueous solution of basic salt of sodium, followed by adjusting the pH to a range between 5 and 9, and removing insoluble substances with heat; and
    3) adding ethanol into the aqueous solution of cefamandole nafate obtained at step 2) at the ratio of 4:6 for ethanol to the secondary purified aqueous solution by volume at the range of temperature between 60 and 100° C., and recrystallizing by cooling gradually down to the range of temperature between room temperature and 10° C.

9. The process for refining cefamandole nafate according to claim 8, characterized in that, the pH in step 1) is decreased after said cefamandole nafate passes through the acidic ion exchange resin.

10. The process for refining cefamandole nafate according to claim 8, wherein the basic salt of sodium used in step 2) is one or more selected from a group consisting of sodium carbonate, sodium bicarbonate, sodium formate, sodium acetate, sodium propionate and sodium benzoate.

11. The process for refining cefamandole nafate according to claim 10, wherein the basic salt of sodium used in step 2) is sodium carbonate or sodium acetate.

12. The process for refining cefamandole nafate according to claim 8, characterized in that, the temperature at which insoluble substances are removed with heat is from 30 to 90° C.

13. The process for refining cefamandole nafate according to claim 8, wherein removing the water retained in the cefamandole nafate of step 3) during the temperature raised from 60 to 100° C. by vaporizing.

* * * * *